(12) United States Patent
Yankov (10) Patent No.: US 7,889,336 B2
(45) Date of Patent: Feb. 15, 2011

(54) OPTICAL INTEGRATED NANOSPECTROMETER

(76) Inventor: Vladimir Yankov, 280 S. Chestnut St., Washington Township, NJ (US) 07676

(*) Notice: Subject to any disclaimer, the term of this patent is extended or adjusted under 35 U.S.C. 154(b) by 429 days.

(21) Appl. No.: 12/012,045

(22) Filed: Feb. 1, 2008

(65) Prior Publication Data
US 2009/0195778 A1 Aug. 6, 2009

(51) Int. Cl.
*G01J 3/28* (2006.01)
*G01J 3/44* (2006.01)
*G02B 6/12* (2006.01)

(52) U.S. Cl. .................... 356/328; 356/301; 385/14; 385/32

(58) Field of Classification Search .......... 356/328, 356/301; 385/10–37, 129, 132; 372/18, 372/20, 96, 102; 398/84
See application file for complete search history.

(56) References Cited

U.S. PATENT DOCUMENTS

| | | | |
|---|---|---|---|
| 4,923,271 | A | 5/1990 | Henry et al. |
| 6,707,047 | B2 | 3/2004 | Craig et al. |
| 7,054,517 | B2* | 5/2006 | Mossberg et al. ............ 385/14 |
| 7,120,334 | B1 | 10/2006 | Mossberg et al. |
| 7,330,614 | B1* | 2/2008 | Mossberg et al. ............ 385/14 |
| 2005/0151966 | A1 | 7/2005 | Packirisamy et al. |
| 2006/0255255 | A1 | 11/2006 | Miller et al. |

FOREIGN PATENT DOCUMENTS
CN 1350165 5/2002

OTHER PUBLICATIONS

Hamamatsu Photonics Co., Ltd. (http://sales.hamamatsu.com/assets/pdf/parts_C/c9407ma) etc_kacc1136e0.pdf) produces compact spectrometers of traditional configuration for ultraviolet, visible, and near-infrared spectral bands.
Ocean Optics (http://www.oceanoptics.com/products/usb2000+.asp), produces compact spectrometers of traditional configuration for ultraviolet, visible, and near-infrared spectral bands.
Vladimir Yankov, et al. "Multiwave-length Bragg Gratings and Their Application to Optical MUX/DEMUX Devices", Photonic Technology Letters, vol. 15, pp. 410-412, 2003.
S. Grabarnik, et al. Miniature spectrometer. "Optics Express", vol. 15, No. 6, pp. 3581-3588, 2007.
A. Bross Investigation of the use of CCDs as high-resolution position-sensitive detectors of ionizing radiation (Lawrence Berkeley Laboratory) (http://www.slac.stanford.edu/cgi-wrap/getdoc/icbp82-009.pdf).

* cited by examiner

*Primary Examiner*—Sang Nguyen (57) ABSTRACT

A planar nanospectrometer formed as a single chip that uses diffraction structures, which are combinations of numerous nano-features placed in a predetermined configuration and providing multiple functionalities such as guiding light, resonantly reflecting light at multiple wavelengths, directing light to detectors, and focusing light on the detectors. The diffraction structure can be described as a digital planar hologram that comprises an optimized combination of overlaid virtual sub-gratings, each of which is resonant to a single wavelength of light. Each device includes at least one sensor, at least one light source, and at least one digital planar hologram in an optical waveguide. The device of the present invention allows detection of small amounts of analytes in gases and liquids or on solid surfaces and can be particularly advantageous for field analysis of environmental safety in multiple locations because of its miniature size and low cost.

19 Claims, 9 Drawing Sheets

OPTICAL INTEGRATED NANOSPECTROMETER

CROSS REFERENCE TO RELATED APPLICATIONS

The present patent application is related to the following patent applications: (1) U.S. patent application Ser. No. 10/405,160, now abandoned; filed by V. Yankov et al on Apr. 2, 2003 entitled "Planar holographic multiplexer/demultiplexer"; (2) U.S. patent application Ser. No. 10/137,152, now abandoned; filed by S. Babin et al on May 2, 2002 entitled: "Photonic multi-bandgap lightwave device and methods for manufacturing thereof"; and (3) U.S. patent application Ser. No. 10/167,773, now abandoned; filed by L. Polonskiy et al on Jun. 11, 2002 entitled: "Integrating elements for optical fiber communication."

FIELD OF THE INVENTION

The present invention generally relates to optical spectrometry for detecting small quantities of analytes and for other related applications. In particular, the present invention provides a miniature integrated optical spectrometer based on nano-structures embedded into planar waveguides.

BACKGROUND INFORMATION

Last century witnessed multiple improvements in optical spectrometer design and dramatic reduction in size. As a result, spectrometers have moved from optical laboratories to industrial, field, aerospace and other areas of application where compactness, ruggedness, reliability, and low cost are crucially important.

Several companies supply compact spectrometers of traditional configuration for ultraviolet, visible, and near-infrared spectral bands. For example, two such companies are Hamamatsu Photonics Co., Ltd. and Ocean Optics (see links below); however, new achievements in nanotechnology make it possible to develop even smaller spectral devices.

For example, U.S. Pat. No. 4,923,271 to Henry et al ("Henry") issued on May 8, 1990 describes an optical multiplexer/demultiplexer comprising cascaded elliptic Bragg reflectors (gratings). All gratings are formed by means of microlithography in a planar waveguide. Each grating is tuned to a definite light wavelength corresponding to one of the working channels. The gratings have one common focal point but different elliptical ties so that the location of the remaining focus can be chosen to provide adequate spacing between input and output. Preferably, the plurality of elliptical Bragg gratings is ordered such that the grating associated with the shortest wavelength is positioned closest to the input of the device. In principle, this type of optical chip can be used as a spectral device for limited amount of wavelengths; however, extending this type of optical chip to a large number of channels is not feasible, and this is the main disadvantage of the approach. The gratings are separated spatially for sequential processing of light. As the number of channels and correspondingly the number of wavelengths to be processed grows, the size of the device increases, the path of light to the remote gratings grows, and, consequently, intrinsic losses grow as well. Also, building large devices is difficult and expensive due to limited precision of the lithographic process and limited uniformity of the waveguide used for gratings.

A new approach to spectral planar integrated devices is based on superposition of multiple sub-gratings on the same planar area. Each sub-grating resonates to a fixed wavelength, but a super-grating comprising many sub-gratings can be deployed as a spectral instrument. Several devices and systems based on this new approach are disclosed in several pending U.S. Patent Applications such as U.S. patent application Ser. No. 10/405,160 filed by V. Yankov et al on Apr. 2, 2003 entitled "Planar holographic multiplexer/demultiplexer"; U.S. patent application Ser. No. 10/137,152 filed by S. Babin et al on May 2, 2002 entitled "Photonic multi-bandgap lightwave device and methods for manufacturing thereof"; U.S. patent application Ser. No. 10/167,773 filed by L. Polonskiy et al. on Jun. 11, 2002 entitled "Integrating elements for optical fiber communication." However, none of these publications discloses how the new approach can be introduced into the structure of a spectrometer.

The overlaying of multiple sub-gratings for optical multiplexer/demultiplexer applications was further developed by Vladimir Yankov et al as disclosed in "Multiwavelength Bragg Gratings and Their Application to Optical MUX/DEMUX Devices," Photonic Technology Letters, vol. 15, pp. 410-412, 2003.

Based on the above principle, several optical systems were patented by Thomas Mossberg et al (see U.S. Pat. No. 7,120,334 issued on Oct. 10, 2006 entitled "Optical Resonator Formed in a Planar Optical Waveguide with Distributed Optical Structures." However, the inter-laser cavity spectrometer proposed by T. Mossberg in U.S. Pat. No. 7,120,334 has a narrow band limited by laser spectral properties and a cavity-free spectral range, works only on the absorption principle, and analyzes only liquids. The remaining two patents do not teach a compact spectrometer.

S. Grabarnik et al reported information on a miniature spectrometer with a volume of 0.135 $cm^3$ and dimensions of 3×3×11 mm mounted directly on the surface of a charge-coupled device (CCD) sensor (see *Optics Express*, Vol. 15, No. 6, pp. 3581-3588, 2007). The spectrometer is formed by two flat diffraction gratings that are designed to perform both the dispersion and imaging functions, eliminating the need for spherical optics. Two separate parts of the device were fabricated with single-mask 1/Jm lithography on a single glass wafer. The wafer was diced, and the device was assembled and directly mounted onto a CCD sensor. The resolution of 3 nm, spectral range of 450 to 750 nm, and the optical throughput of ~9% were measured to be in a complete agreement with the model used for development of the device.

In "Investigation of the use of CCDs as high-resolution position-sensitive detectors of ionizing radiation (Lawrence Berkeley Laboratory)", A. Bross reported successful use of charge-coupled devices (CCDs) as analog shift registers, optical imagers, and high-density memories. In fact, the device comprises a CCD Planar spectrometer operable in either one- or two-dimensional modes.

A common disadvantage of the above-described known optical spectrometers is their relatively large dimensions, and the applicants are unaware of the existence of miniature optical planar spectrometers designed and operating on the principle of digital planar holography.

SUMMARY OF THE INVENTION

An object of the present invention is to provide a nanospectrometer on the basis of digitally generated diffraction structures in planar optical waveguides. Another object of the invention is to provide a method of manufacturing the aforementioned nanospectrometer by means of microlithography. It is a further object to provide a nanospectrometer with super-gratings that comprise multiple overlaid sub-gratings consisting of standard binary features such as dashes or grooves etched or formed in a planar waveguide by means of microlithography.

The nanospectrometers of the invention use diffraction structures, which are combinations of numerous nano features placed in a configuration and providing multiple functionalities such as guiding light, resonantly reflecting light at multiple wavelengths, directing light to detectors, and focusing light on detectors. A diffraction structure can be described as a super-grating because it is an optimized combination of overlaid sub-gratings, each of which is resonant to a single wavelength of light. Each device includes at least one sensor, at least one light source of spectrum, at least one super-grating in an optical waveguide, and at least one array of detectors. In other words, the super-grating works as a high-resolution diffractive element.

The device of the present invention allows detection of small amounts of analytes in gases and liquids or on solid surfaces and can be particularly advantageous for field analysis of environmental safety in multiple locations because of its miniature size and low cost.

For successful development of nanospectrometers it is crucially important to properly design their dispersive elements, i.e., super-gratings. The super-grating comprises multiple sub-gratings, which consist of standard binary features like dashes, or grooves, etched or otherwise formed in a planar waveguide in order to generate local modulations of effective refractive index inside a planar optical waveguide. Positions of standard features are determined by a generating function, which is calculated based on desired parameters of the super-grating. Essentially, these gratings are sets of zeroes and ones engraved on the planar waveguide. A typical grating consists of several million features, which could be used in huge number of combinations, but only a few of them are appropriate for efficient operation; therefore, it is necessary to optimize the generating function.

According to the present invention, each super-grating is generated as a mathematical superposition of elliptic, parabolic, or hyperbolic sub-gratings with a spatial period of approximately one-half wavelength by a method characterized by the following steps. The first to be created is a two-dimensional analog-generating function $A(x,y)$ representing a superposition of modulation profiles of the refractive index. Each modulation function corresponds to the equivalent of a sub-grating. Determined in this step is a two-dimensional generating function $A(x,y)$, which resembles an interference pattern of wavelengths emitted from multiple sources at different wavelengths. The generating function $A(x,y)$ is a mathematical linear superposition of integration of elliptic sub-gratings, wherein each sub-grating is tuned to resonantly reflect at one of the N spectral channels.

The next step is binarization of a two-dimensional analog-generating function $A(x,y)$, which was produced in the previous step. Binarization is achieved by applying a threshold value and assigning 1 to all areas above the predetermined threshold and 0 to the remaining areas in order to obtain a digital two-dimensional generating function $B(x,y)$.

Next, the complex shape islands in $B(x,y)$ with the value of 1 are simplified in order to be presented as a combination of standard microlithographic features (short straight lines and dashes). This is accompanied by conversion to function $C(x,y)$.

The last step is lithographic fabrication of the calculated standard microlithographic features by etching all binary features as function $C(x,y)$ to a calculated depth on a planar waveguide.

The present invention further provides the step of applying an apodization function to a function representing a plurality of binary features to be written by using single-layer (binary) microlithography. This is necessary in order to suppress side lobes of the transfer function. In particular, according to the present invention, an apodization function $g(r)$ is determined and applied to binary features by removing some of the binary features to the extent that an average density of the binary features becomes proportional to $g(r)$.

The present invention further provides the step of correcting crosstalk by imposing a linear relationship on geometrical positions of input/output ports and central frequencies of channels. According to another modification of the present invention, crosstalk can be suppressed by precompensation of generating function $A(x,y)$.

With use of the above-described super-grating, the present invention makes it possible to develop nanospectrometers of different types that can be integrated on a chip for detection of solid, liquid, or gas analytes. Examples of these nanospectrometers are the following: a laser-induced breakdown (LIB) spectrometer, an absorption spectrometer, or a Raman spectrometer.

DETAILED DESCRIPTION

In the context of the present invention, the term "super-grating" means a digital planar hologram that performs multiple functions and operates for a plurality of channels incorporated into a nanospectrometer.

In the context of the present invention, the term "sub-grating" means a virtual component of the aforementioned digital planar hologram that provides operation of a single light-signal-transmitting channel. The same elements of different sub-gratings belong to the same super-grating.

The physics of a spectral super-grating, deployed in the invented spectrometers, is complicated, and for this reason several theoretical models should be used to explain the properties of transfer function. In a first approximation, the super-grating works like a superposition of elliptical sub-gratings, each of which connects an input port with one of multiple output ports. The sub-gratings are structures that are composed of multiple nano-features that modulate the refractive index of a planar waveguide where propagating light is confined. The nano-features are positioned in a manner to provide resonant reflection of light of a predefined wavelength. The super-grating works like a superposition of sub-gratings, reflecting multiple wavelengths to assigned output ports. The super-grating is designed for monitoring specific wavelengths where the wavelengths of interest are prerecorded in the features of the hologram.

The super-grating can be also considered as a photonic bandgap quasi-crystal with a quasi-periodic structure and multiple periods corresponding to multiple bandgaps. In such devices, light propagates in any direction except specifically designed one, thus resulting in light reflection from one ellipse focus into another. These photonic bandgap quasi-crystals can be made by means of binary lithography, nano-imprinting, or other methods on planar waveguides and contain nano-features that modulate the refractive index, and are made for example, into the form of dashes.

The super-grating is synthesized from multiple overlaid sub-gratings in a synergistic manner, which includes a mathematical superposition of modulation functions followed by binarization. This process is substantially different from direct superposition of sub-gratings because superposition originates as a mathematical step, which effectively averages a plurality of modulation functions having varying phases.

As discussed above, the nano-features form a predetermined planar quasi-periodic pattern of the refractive index. Positions of features are chosen to optimize transfer functions of all wavelengths.

According to the present invention, each super-grating is originally computed as a mathematical superposition of elliptic, parabolic, or hyperbolic sub-gratings with a spatial period of approximately one-half wavelength, for which this sub-grating will be resonant (reflective). An analog-generating function A(x,y) that describes modulation of the refractive index in a planar waveguide and resembling a superposition of a plurality of interference fringes of diverging and converging light beams is implemented according to the following expression:

$$A(x, y) \sim \sum_{i=1}^{i=N} a_i \mathrm{Sin}(2\pi(1 + f(x, y))l_i / \lambda_i + \varphi_i), \quad (1)$$

where index i refers to a wavelength number as well as corresponding output port:

$$l_i = |\vec{r}_i^{\,in}| + |\vec{r}_i^{\,out}|,$$

where:

$\vec{r}_i^{\,in}$ is a vector connecting the input port to an arbitrary point (x,y) on the planar surface;

$\vec{r}_i^{\,out}$ is a vector that connects this point with coordinates (x,y) to the output port i for a chosen wavelength $\lambda_i$;

$a_i$ is a weight coefficient associated with wavelength i; and $\phi_i$ is an arbitrary phase associated with wavelength; and $f(x,y)$ is a function that compensates for variation of refractive index.

(All of the parameters above are associated with wavelength $\lambda_i$.)

The generating function A(x,y) is a mathematical linear superposition of integration of elliptic sub-gratings, wherein each sub-grating is tuned to resonantly reflect at one of the N spectral channels. The A(x,y) function resembles holographic fringes with an omitted factor 1/r to avoid performance deterioration. A super-grating with variation of the effective refractive index n(x,y) described by the analog generating function $$A(x,y)n(x,y) \sim A(x,y) \quad (2)$$

would have the best performance, but, unfortunately, it cannot be fabricated by mass production technologies (microlithography, nano-imprinting, or the like). In planar waveguide technology, the analog-generating function A(x,y) can be implemented as its surface relief. This will modulate the effective refractive index as prescribed by formula (1), but fabricating that multilevel relief with modern lithography is very difficult if possible at all.

Therefore, to make this approach practical, the relief must be reduced to a binary shape, meaning that there cannot be more than one nano-feature at each location. According to the present invention, this problem is solved by approximating the analog-generating function A(x,y) into a binary function B(x, y). However, since the binary function B(x, y) contains complex shape islands, it should be further simplifies by assigning the value of 1 to areas that exceed a predetermined threshold and 0 to all the remaining areas in order to present the binary function B(x, y) as a combination of standard microlithographic features for conversion to discrete generating function C(x,y).

In other words, in order to obtain a digital (binary) two-dimensional generating function B(x,y), binarization of function A(x,y) is further implemented by applying a threshold value by assigning 1 to all areas above the predetermined threshold and 0 to the remaining areas. For further simplification of manufacturing conditions with the use of microlithography and nano-imprinting techniques, the shape of function B(x,y) is simplified by replacing ditches with curved boundaries by a combination of standard microlithographic nano-features (short straight grooves or dashes). This operation can be described as quantization of binary function B(x, y) to produce a discrete function C(x,y), which is nothing but a collection of standard nano-features (dashes) that can be formed according to the aforementioned mass-production methods.

The super-grating described by the discrete generating function C(x,y) preserves all spectral properties of the original analog-generating function A(x,y), but binarization and quantization could introduce additional artifacts. Therefore, careful approach and thorough optimization of conversion algorithms are required.

The last parameter of the super-grating to be determined is the depth of dashes to be formed in a planar waveguide by microlithography or nano-imprinting.

Figure 1:
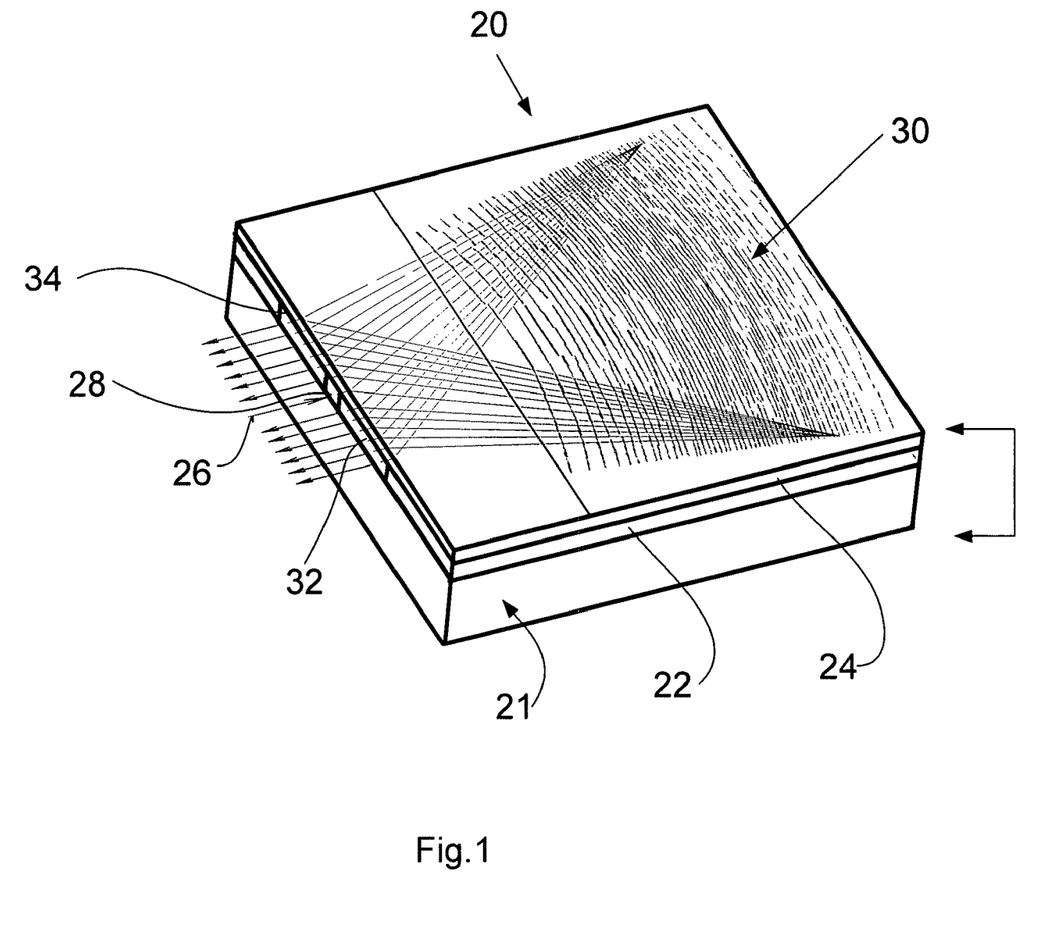
FIG. 1 illustrates an exemplary super-grating embedded into a planar waveguide according to one modification of the present invention.

FIG. 1 illustrates an exemplary nanospectrometer 20 having an integrated super-grating 30 with a planar waveguide 31 that comprises several flat layers of transparent optical materials, each associated with different refraction indices. The materials are chosen so that one of them, referred to herein as the core 24, has a refractive index, which is higher than the refractive indices of the cladding 22. This provides a low-loss guiding of lightwaves through the core 24.

In the exemplary modification shown in FIG. 1, an input light signal 26 comprising multiple wavelengths to be spectrally analyzed enters the planar waveguide 31 through an input port 28 from an optical fiber or from a ridge waveguide (not shown in FIG. 1) and propagates within a sector determined by the angular aperture of the input port. The super-grating 30 that incorporates multiple nano-features organized according to discrete generating function C(x,y) is embedded into one or more layer interfaces of the waveguide. The super-grating 30 works as a thick (volume) digital hologram directing light of various wavelengths to the assigned output ports 32 and 34.

Figure 2:
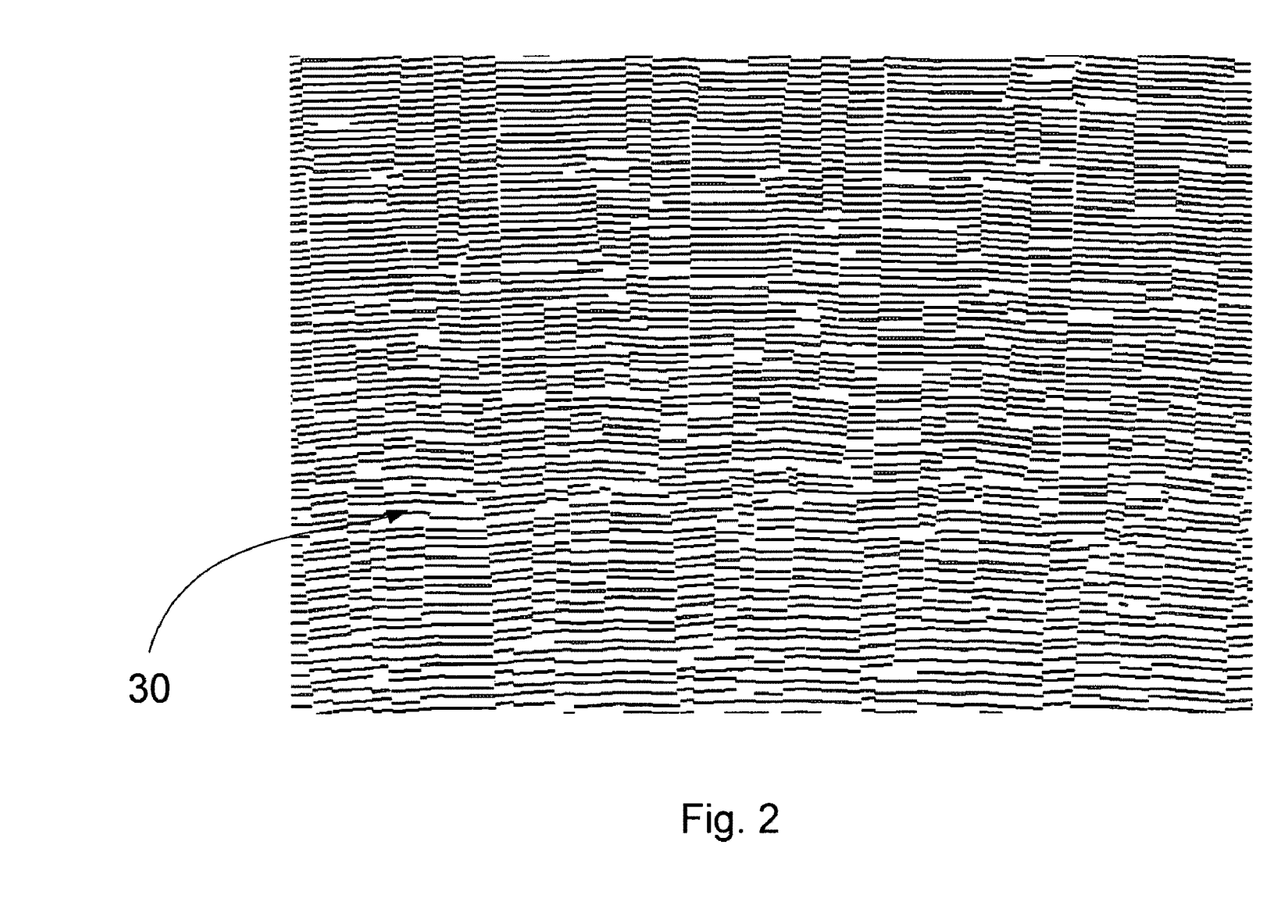
FIG. 2 illustrates a fragment of an exemplary realization of a function $C(x,y)$ for a super-grating with eight resonant wavelengths made in accordance with the invention.

FIG. 2 illustrates a fragment of an exemplary realization of discrete generating function C(x,y) for an eight-channel super-grating 36 (dark lines that represent grooves etched on the layer interface(s) of the waveguide). This super-grating 36 resonantly reflects eight various wavelengths to the assigned output ports 32 and 34 (FIG. 1).

Figure 3A:
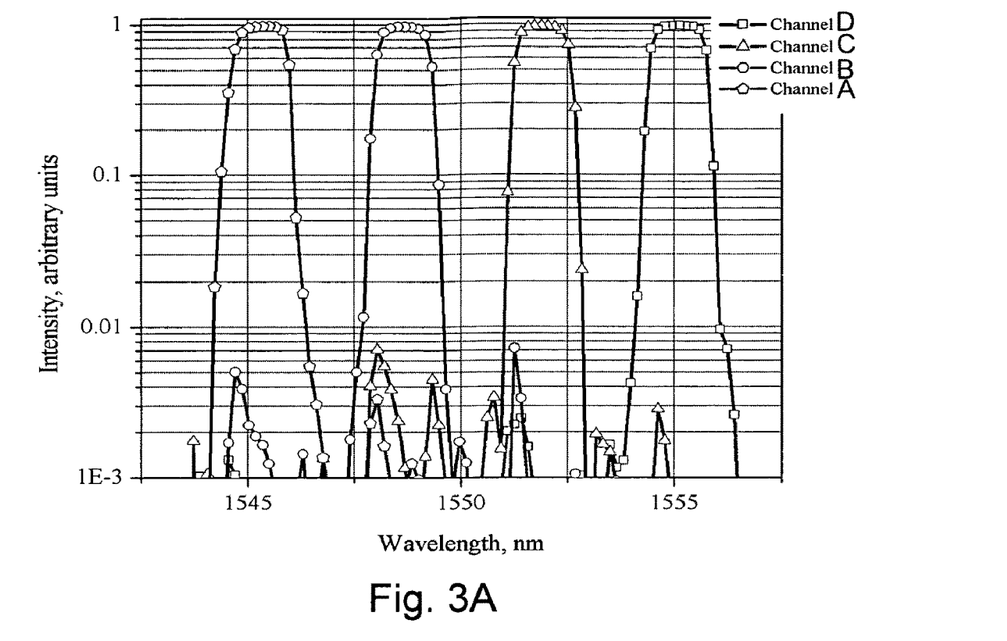
FIG. 3A shows the simulated transfer function for a 4-channel PBQC according to the invention.
Figure 3B:
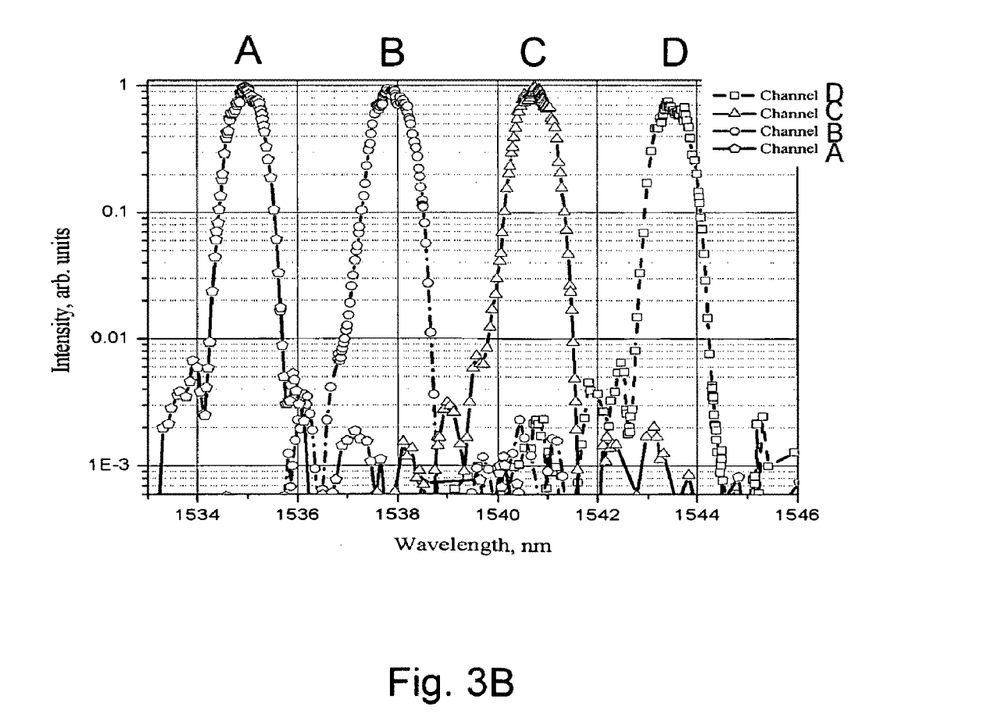
FIG. 3B shows the transfer function for the same device as in FIG. 3A, measured experimentally.

An example of practical implementation of this invention is demonstrated in FIGS. 3A and 3B. FIG. 3A shows a simulated transfer function for a four-channel super-grating, while FIG. 3B presents the experimentally measured transfer function of the same super-grating fabricated on a planar waveguide with a core thickness of 0.4 micron and a core refractive index of $n_{core}=1.75$, the core being isolated by a cladding with the refractive index of $n_{clad}=1.44$. In FIG. 3B, the sub-grating (channel) transfer functions are denoted as A, B, C, and D. In FIGS. 3A and 3B, wavelengths (nm) are plotted on the abscissa axis, and the intensity (arbitrary units) is plotted on the ordinate axis. In that case the effective refractive index for the TE mode is about 1.53, for the TM mode about 1.47, and for cladding modes about 1.44. As can be seen, the experimental data substantially coincides with theoretical assumptions described above.

Figure 4A:
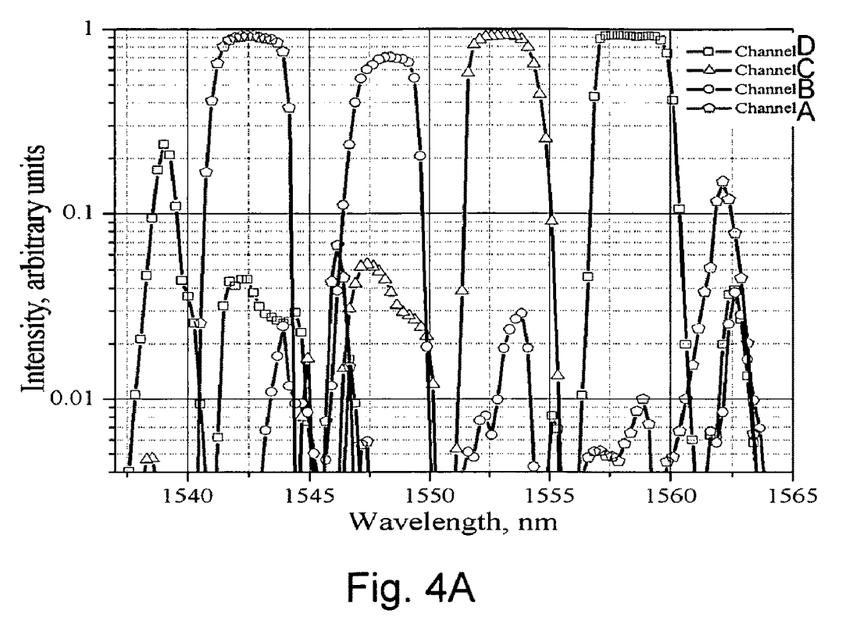
FIG. 4A demonstrates the transfer function of a 4-channel super-grating with low channel isolation (high crosstalk) according to the invention.
Figure 4B:
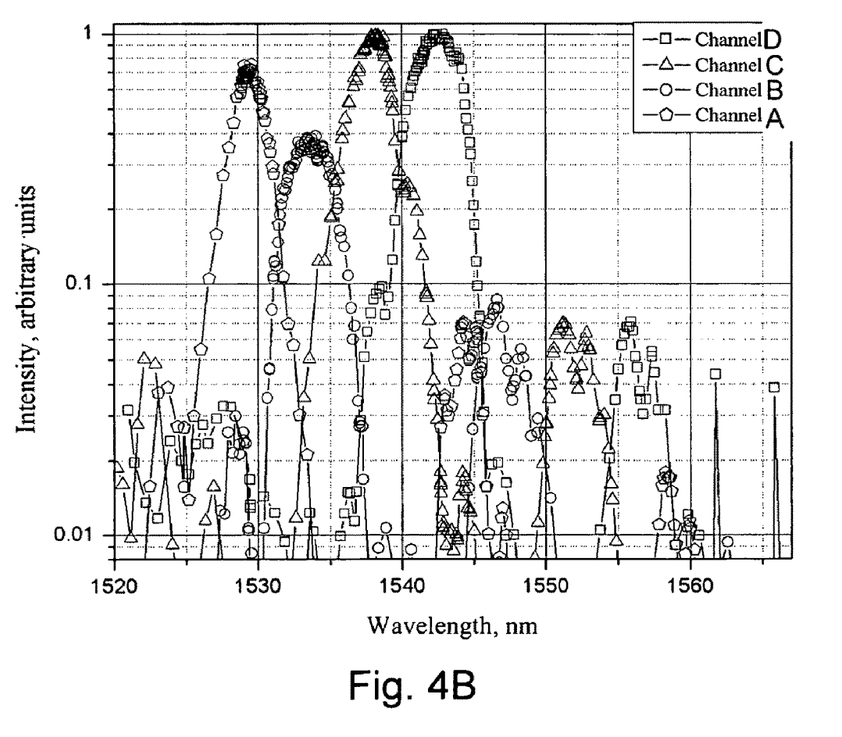
FIG. 4B demonstrates the transfer function for the same device as in FIG. 4A, measured experimentally.

According to the present invention, optimization of the super-grating design consists of finding an analog-generating function A(x,y) that provides best possible performance for the super-grating after the aforementioned binarization and quantization procedures. The most dangerous and performance-degrading effect is crosstalk between the super-grating channels, which may be caused by insufficient channel isolation (crosstalk is reflection of light with different frequencies in the same direction). Binarization of the analog-generating function A(x,y) is a strongly nonlinear transform. In accordance with the rules of nonlinear transform, if A(x,y) includes just three Fourier components with wave vectors $\vec{k}_i, \vec{k}_j$ and $\vec{k}_h$, the Fourier spectrum of the generated binary relief would include the beating-generated wave vectors $\vec{k}^b_{ijh}$ expressed by a linear combination of the three original wave vectors:

$$\vec{k}^b_{ijh} = m\vec{k}_i + n\vec{k}_j + l\vec{k}_h, \qquad (3)$$

where m, n, and i are arbitrary positive or negative integers. These parasitic Fourier harmonics may be responsible for high crosstalk (insufficient channel isolation). In fact, this effect was observed both in simulations and experiments, as illustrated in FIG. 4A (simulation) and FIG. 4B (experiment). In FIGS. 4A and 4B, the wavelengths (nm) are plotted on the abscissa axis, and the intensity (arbitrary units) is plotted on the ordinate axis. The transfer function of a four-channel super-grating demonstrates high crosstalk and low channel isolation about 8 dB only, while it is typically required that isolation be not less than 25 dB.

If for simplicity of consideration we approximate each channel by a single $\vec{k}$ and take into account that the wave vectors of close channels have almost the same values, then combinations of formula (3) with m and n having values equal or close to 1 and −1, respectively, e.g., those expressed by $$\vec{k}_i + (\vec{k}_{i+1} - \vec{k}_{i+2}) \approx \vec{k}_i \qquad (4)$$

will become close to one of the original wave vectors $\vec{k}$ and will reflect light of a different wavelength (another channel) to the output port assigned for $\vec{k}$. Additional analysis shows that the reflections are focused. Therefore, such approximation will increase the crosstalk to an unacceptably high level.

Figure 5:
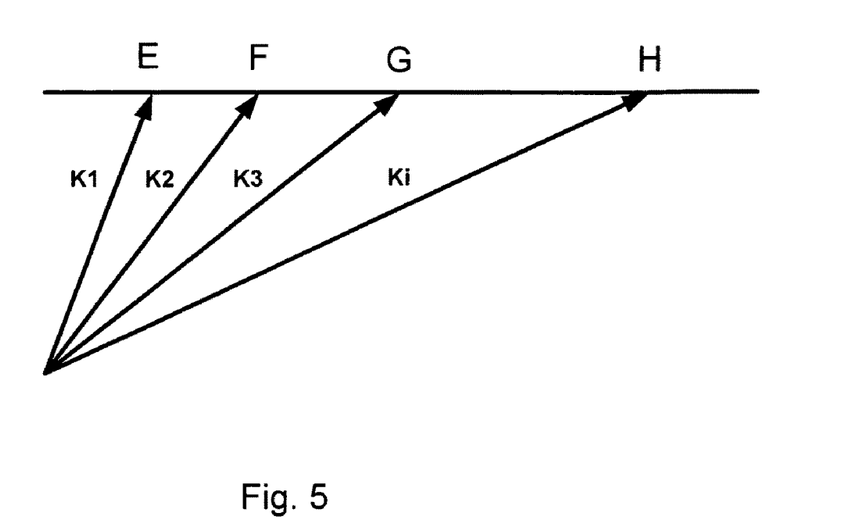
FIG. 5 shows the wave vectors of sub-gratings participating in the synthesis of a super-grating made in accordance with the invention.

In accordance with the present invention, the above problem can be solved by properly positioning the output ports. Let us assume now that at some point the directions of wave vectors vary with absolute value of sub-grating wave vectors linearly so that the tips of the vectors lie on a straight line, as shown in FIG. 5, where E, F, G, and H are the wave vectors of channel sub-gratings. In this case, any linear combination of wave vectors lies on the same straight line that is frequency of reflected light is a function of reflection direction and, consequently, crosstalk is avoided. [is unclear as written.] If the foci positioning is linear and coordinates of output ports $R_i$ satisfy the following equation:

$$\vec{R}_i = \vec{R}_0 + \delta\vec{R} \cdot \omega_i \qquad (5)$$

where $\omega_i$ is the central frequency of the channel, then, in approximation of a small numerical aperture and small sub-grating ellipticity, the wave vectors of the channel sub-gratings will lie on straight lines, as shown in FIG. 5. The positions of the input port as well as channel spacing are arbitral. It is understood that the input port receives light having specific spectral characteristics or a spectrum obtained from a light source, which is not shown in FIG. 1. This procedure of correcting binarization nonlinearity by properly positioning the channel was confirmed by both simulations and experiments, as shown in aforementioned FIG. 3A (simulation) and 3B (experiment). It can be seen that the aforementioned correction provides channel isolation of 28 dB, which is almost 20 dB better than without the aforementioned correction.

Another source of artifacts is substitution of an infinite-size periodic structure with a finite one having sharp edges. This leads to appearance of additional Fourier harmonics and, thus, additional out-of-band reflections. Such a problem is well known in the theory of fiber Bragg gratings. The remedy, which consists of smoothening (apodization) of the back and front ends of the grating, is known as well. Usually, the grating apodization leads to gradual variation of the refractive index modulation depth in accordance with a certain (apodizing) function g(r), where r is the distance to the input point (where light enters the grating). Inside the apodized super-grating the modulation function smoothly grows in a central zone of the super-grating from zero (no n(x,y) modulation) to unit (maximum n(x,y) modulation) and then slowly drops to zero at its end. Full-scale modulation occurs only in the central part of the super-grating, which is surrounded with areas of variable modulation depth to provide a smooth transition from a nonmodulated to a fully modulated refractive index. Because the present invention uses binary nano-features, apodization can be implemented by removing some nano-features in the transitional areas so that the average density of the binary nano-features becomes proportional to g(r).

In the next step, a compensation function is applied in order to compensate for variations in the average refractive index. In particular, a digital planar hologram creates a variation of the average effective refractive index so that the light wavelength within the digital planar hologram differs from that within the blank part of a planar waveguide. To avoid undesirable distortions due to this nonuniformity, it is necessary to compensate [for] the refractive index variation caused by patterning the planar waveguide, including variation caused by apodization. According to one modification of the present invention, a compensation function can be defined by the following equation:

$$f(x,y)=1+\Delta n/n=1+ag(r), \quad (6)$$

where $\Delta n$ is the averaged variation of the effective refractive index in the vicinity of a given point, a is the scaling parameter, and r is the distance to an input port.

Figure 6:
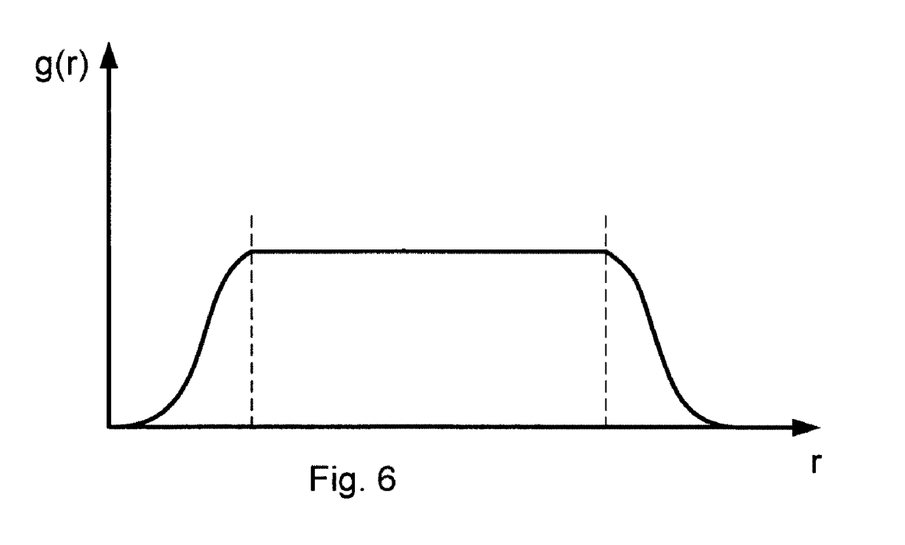
FIG. 6 illustrates the grating apodization function $g(r)$ formed by the method of the invention.

The super-grating apodization is illustrated in FIG. 6, where 23 and 25 are transitional areas and 24 is the central super-grating zone with the area of maximum modulation of the planar waveguide refractive index.

The super-grating is the main component of any nanospectrometer made in accordance with the present invention; however, as explained below, in order to improve functionality, the spectrometer should include some additional components. It should be understood that depending on the proposed nanospectrometer configuration, all or almost all components will be integrated on the same planar waveguide as the super-grating.

Figure 7:
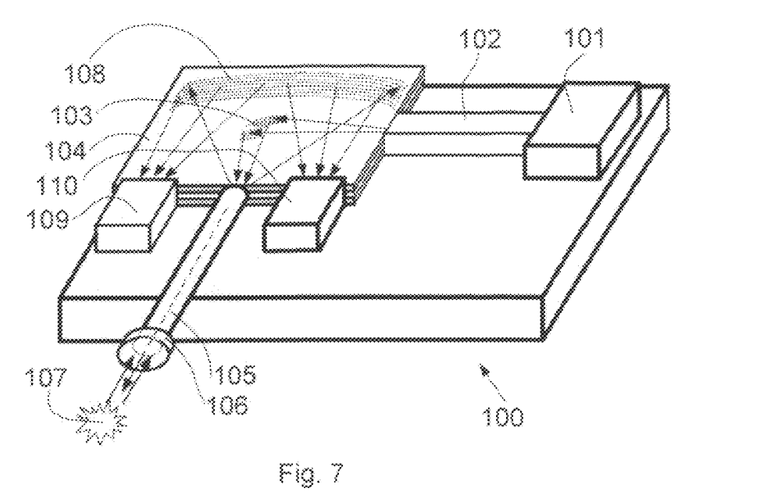
FIG. 7 shows the configuration of the laser-induced breakdown (LIB) nanospectrometer corresponding to the present invention.

The first configuration of the nanospectrometer is a laser-induced breakdown (LIB) spectrometer, shown in FIG. 7. The LIB nanospectrometer is integrated on a base 100, which can be a piece of silicon wafer or any other substance appropriate for attaching all components. The super-grating 108 is embedded into a planar waveguide 104. A laser 101 is integrated on the same base 100 and is coupled with a ridge waveguide 102, which, in turn, is coupled with the planar waveguide 104 so that the laser beam propagates directly to a narrowband concave grating 103. This grating is embedded into the same planar waveguide 104 and is implemented as a sub-grating component of the super-grating with the function to reflect and focus the laser beam for coupling it into an optical fiber 105. The laser beam is delivered by the fiber to an object having a solid or liquid surface 107, which needs to be studied and on which the laser beam must be focused through an optical focusing lens 106.

In a small focus, the laser intensity gets high enough to ionize the superficial layer on the surface of the object, and the created plasma emits optical radiation, the spectrum of which is a unique determinant for the ionized substance. This optical radiation is acquired with the focusing lens 106 and is coupled back to the fiber 105, which delivers it to the super-grating 108 for analysis. The super-grating separates light into channels and focuses them on the arrays 109 and 110 of detectors for converting them into electrical signals that can be displayed and processed.

Figure 8:
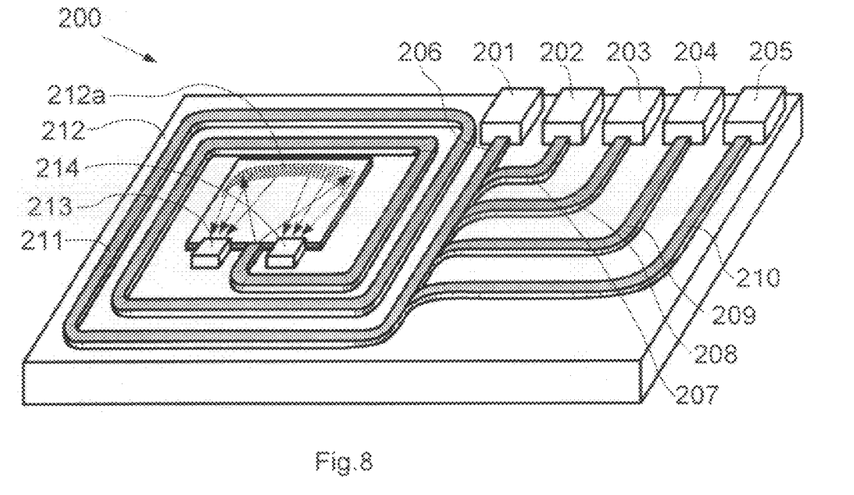
FIG. 8 shows the configuration of the absorption nanospectrometer of the invention with multiple super-luminescent diode light sources.

In the second modification, the device is made as an absorption nanospectrometer, as shown in FIG. 8. All spectrometer components are integrated on a single chip. The device comprises a base 200, which can be a piece of silicon wafer or any other substance appropriate for attaching all components, several super-luminescent laser-emitting diodes (SLED) 201, 202, 203, 204, and 205, which radiate in various spectral bands in order to cover the spectral range appropriate for absorption analysis. All SLEDs are coupled at a point of coupling with ridge waveguides 206, 207, 208, 209, and 210 into a bare ridge guide 211. The ridge guide is referred to as "bare" because it does not have the upper cladding that provides better interaction with the environment and higher sensitivity. The bare waveguide spirals around the chip to accumulate a longer length for better sensitivity and is coupled into a slab waveguide 212 where the super-grating 212a is embedded. Light, analyzed by the super-grating, is focused on arrays 213 and 214 of detectors for conversion into electrical signals, which can be displayed and processed. This nanospectrometer can analyze liquids and gases.

Figure 9:
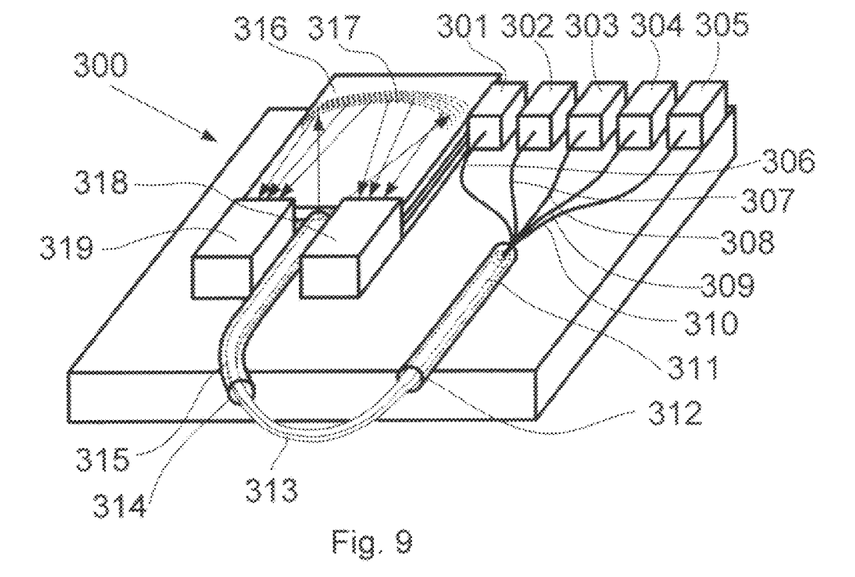
FIG. 9 demonstrates the absorption nanospectrometer of the invention with a bare fiber probe.

The third modification, which is shown in FIG. 9, provides an absorption nanospectrometer with a fiber sensor. This nanospectrometer is similar to the previous one, but the sensor is implemented as a bare fiber (a fiber without a cladding) rather than as a ridge waveguide on a chip. This provides more convenient access to narrow channels or small gaps. All spectrometer components, in addition to the fiber sensor, are integrated on a single chip. The nanospectrometer comprises a base 300, which can be a piece of silicon wafer or other substance appropriate for attaching all components, several super-luminescent laser-emitting diodes (SLED) 301, 302, 303, 304, and 305, which radiate in various spectral bands in order to cover the spectral range appropriate for absorption analysis. All SLEDs are coupled with ridge waveguides 306, 307, 308, 309, and 310 into an optical fiber, which consists of a core 311 and a cladding 312, which participates in guiding the light. At some distance from the chip, the cladding is removed, and a bare fiber 313 (core only) is used for guiding the light. Removal of the cladding makes the fiber probe more sensitive for detecting environmental gas or determining liquid composition. Before returning to the chip, the bare fiber of a required length (longer length provides better sensitivity) is again coated with a cladding 314. The fiber core 315 is coupled into a slab waveguide 316, where the super-grating 317 is embedded. Light, analyzed by the super-grating 317, is focused on arrays 318 and 319 of detectors for conversion into electrical signals, which can be displayed and processed. This nanospectrometer can analyze liquids and gases by submerging the bare fiber probe into them.

Figure 10:
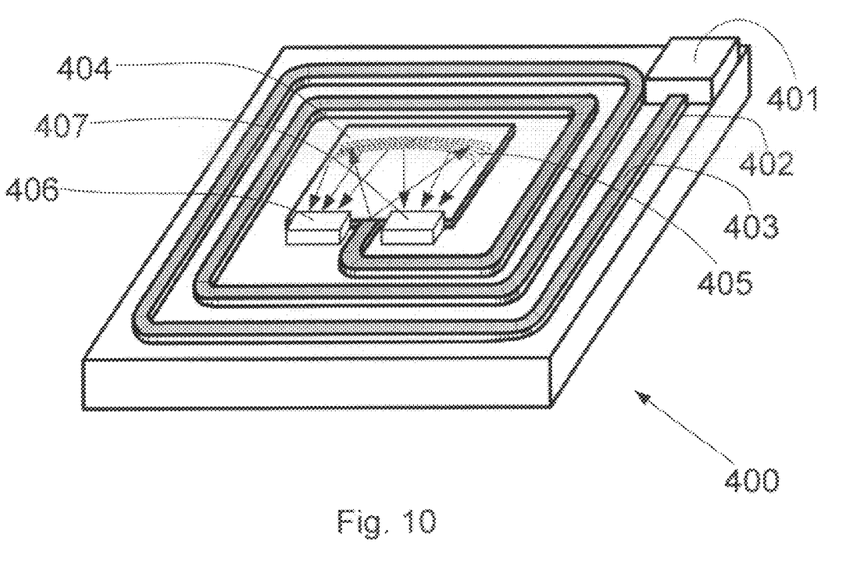
FIG. 10 presents the Raman nanospectrometer on a chip made in accordance with the invention.

The fourth preferred modification, shown in FIG. 10, is a Raman nanospectrometer on a chip. All spectrometer components are integrated on a base 400, which can be a piece of silicon wafer or other substance appropriate for attaching all components. The spectrometer comprises a laser 401 coupled to a ridge waveguide without an upper cladding 402, a spiraling for higher sensitivity around a planar slab waveguide 404 and coupled thereto, a super-grating 405 embedded into the slab waveguide, and arrays 406, 407 of a detector. Deposited on the top of the ridge waveguide 403 is a Raman-enhancing layer 404 comprising nanoparticles of silver or other metal used for increasing the Raman-effect cross-section by many orders of magnitude, typically by $10^9$-$10^{12}$ times and sometimes even more. The laser beam propagates through the ridge waveguide, and each time it reflects from the top, the Raman spectrum caused by the environment is generated. After multiple reflections, the spectrum acquires higher intensity and can be analyzed by the super-grating 405, which is designed to freely transmit the laser wavelength and to focus the Raman spectrum on the arrays of detectors 406 and 407 for converting light signals into electrical signals that can be displayed and processed.

Figure 11A:
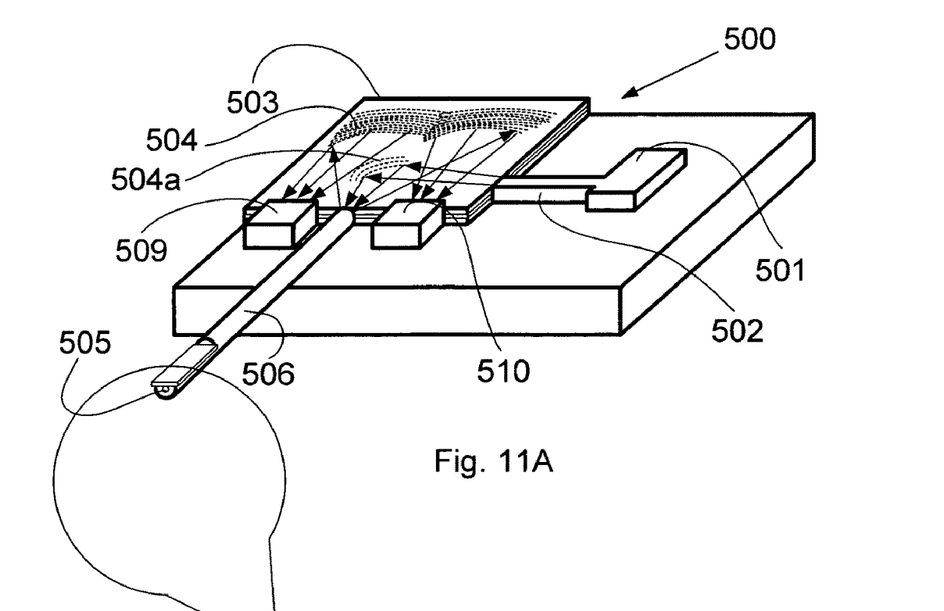
FIG. 11A shows the layout of the Raman nanospectrometer with a fiber probe made in accordance with the invention.
Figure 11B:
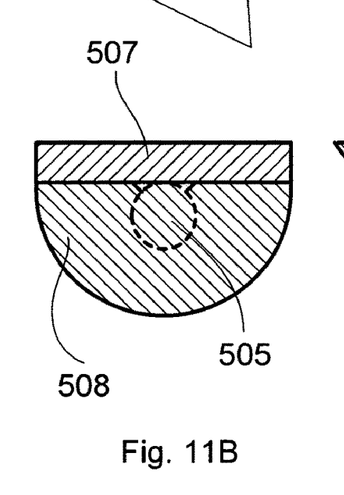
FIGS. 11B through 11C illustrate the shapes of the fiber face used in the spectrometer of FIG. 11A.
Figure 11C:
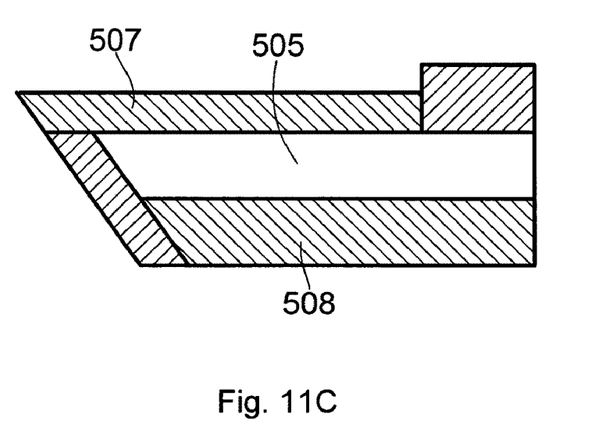

The fifth modification, shown in FIG. 11A, is a Raman nanospectrometer with a fiber probe. All spectrometer components, in addition to the fiber sensor, are integrated on a single chip, which has a base 500 that may be a piece of silicon wafer or other substance appropriate for attaching all components. The spectrometer comprises a laser 501 coupled to a ridge waveguide 502 for guiding laser radiation to a planar slab waveguide 503. The laser beam propagates directly to a narrowband concave grating 504. The grating of this modification is embedded into the same planar waveguide and is implemented as any sub-grating component of the super-grating with the function to reflect and focus the laser beam for coupling it into an optical fiber 506. The laser beam is delivered to the fiber end, which is coated with a Raman-effect enhancing layer 507 that comprises nanoparticles of silver or other metal for increasing the Raman-effect cross-section by many orders of magnitude, typically by an increase of $10^9$-$10^{12}$ times and sometimes even more. For higher sensitivity, the end of the probe is partially stripped of cladding and is made "D-shaped." Shapes of fiber faces that are designated by reference numerals 505, 508, and 507, respectively, are shown in FIGS. 11B to 11C. Such shapes are needed to provide direct contact over a significant area between the Raman-enhancing layer and the fiber probe core 505. In addition, the fiber end is cleaved at an oblique angle to prevent direct reflection of the laser beam back to the chip. After multiple reflections and acquiring the Raman shift, which is the signature of the environment around the probe, the laser beam returns to the chip, where the narrowband mirror reflects the laser wavelength and transmits the Raman-shifted part of the spectrum to a super-grating 504 for analysis.

The super-grating embedded into the slab waveguide 503 focuses the light spectrum on arrays 509 and 510 of the detectors for conversion into electrical signals, which can be displayed and processed.

Figure 12:
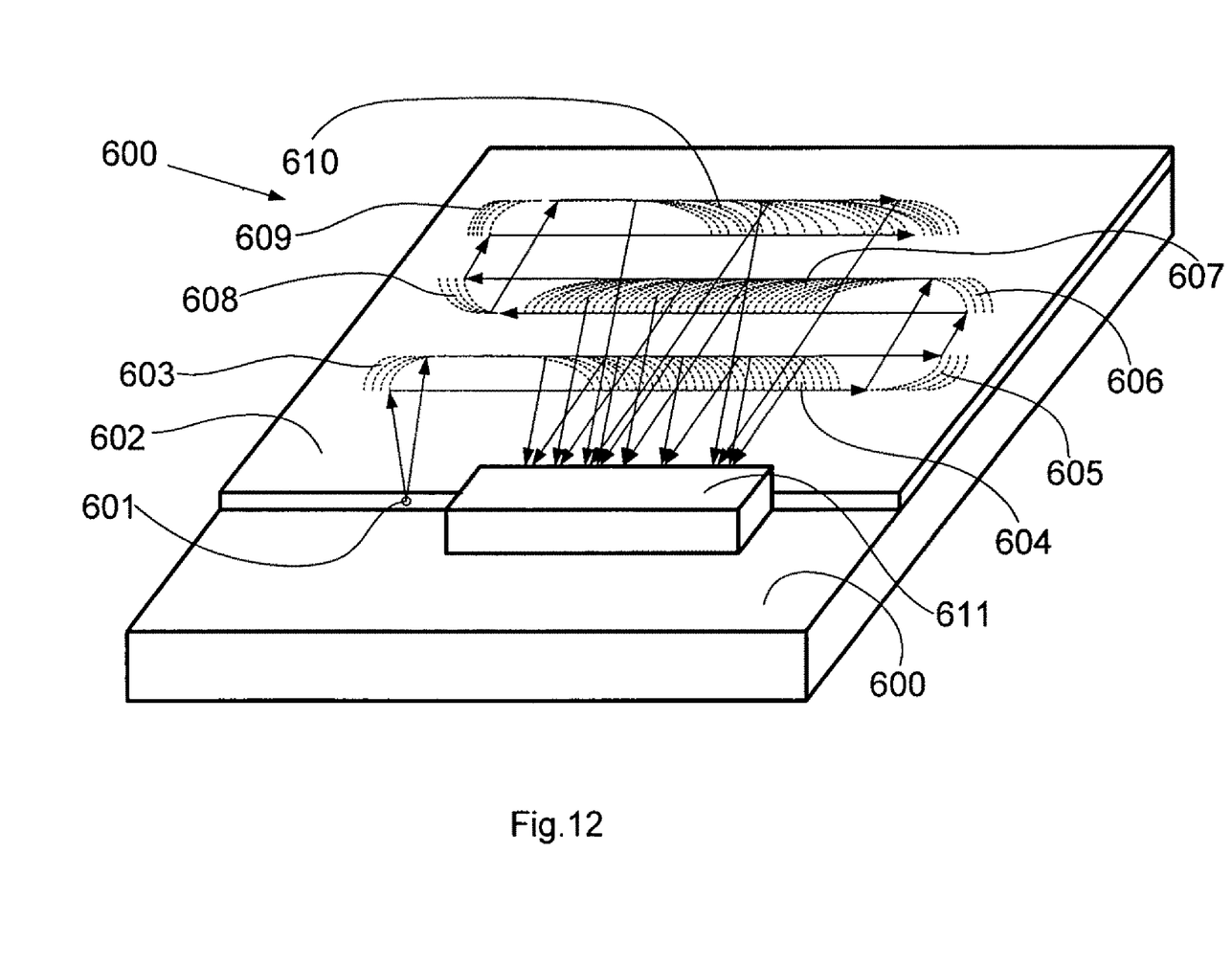
FIG. 12 illustrates a folded nanospectrometer of the invention that has improved resolution.

The sixth preferred modification, shown in FIG. 12, is a folded nanospectrometer of high resolution. The folded layout allows for more compact design and for compensation of optical nonuniformities in a planar waveguide. All spectrometer components are integrated on a single chip that has a base 600, which can be a piece of silicon wafer or other substance, appropriate for attaching the components. The spectrometer comprises an input port 601, from which the light beam to be spectrally analyzed propagates directly to a broadband concave grating 602 that is embedded into the same planar waveguide and operates as a folding mirror. The light beam sequentially goes through the multiple super-grating knees 604, 607, and 610 steered with folding mirrors 605, 606, 608, and 609, all of which are broadband gratings embedded into the same planar waveguide as are the other nanospectrometer components. Each of the super-grating knees reflects spectrally dispersed light to array 611 of the detectors for converting light into electrical signals to be processed, analyzed, and displayed.

Thus it has been shown that the present invention provides a nanospectrometer on the basis of digitally generated diffraction structures in planar optical waveguides. The invention also provides a method of manufacturing the aforementioned nanospectrometer by means of microlithography. The super-gratings of the proposed nanospectrometer comprise multiple sub-gratings consisting of standard binary features such as dashes or grooves etched in the planar waveguide by means of microlithography.

Although the invention has been shown and described with reference to specific embodiments, these embodiments should not be construed as limiting the areas of application of the invention, and any changes and modifications are possible provided these changes and modifications do not depart from the scope of the attached patent claims. For example, optionally, all spectrometers according to the present invention can be used without integrated detector arrays in a spectroscopic mode.

The invention claimed is:

1. An optical integrated nanospectrometer for analyzing an analyte comprising:
   at least one sensor;
   a planar light waveguide with a combination of numerous nano-features placed in a configuration and providing multiple overlaid sub-gratings;
   at least one super-grating embedded into the planar light waveguide; and
   at least one array of detectors for converting light signals into electrical signals supported by the planar light waveguide; wherein the aforementioned super-grating is an optimized combination of the multiple overlaid sub-gratings, each of which is resonant to a predetermined wavelength so that the super-grating inherits all resonances associated with the multiple overlaid sub-gratings and work as a high-resolution diffractive element and wherein the aforementioned super-grating comprises a digital planar hologram.

2. The optical integrated nanospectrometer of claim 1, wherein the digital planar hologram is one obtained from a mathematical superposition of sub-gratings selected from elliptic, parabolic, or hyperbolic sub-gratings that incorporate multiple nano-features embedded into the aforementioned digital planar waveguide.

3. The optical integrated nanospectrometer of claim 2, wherein each of the multiple overlaid sub-gratings is designed to be resonantly reflecting at one of N spectral channels, and wherein the aforementioned nano-features comprise a combination of standard binarized microlithographic features.

4. The optical integrated nanospectrometer of claim 3, wherein the aforementioned standard binarized microlithographic features are straight lines or dashes suitable for lithographic fabrication by etching as discrete generating function C(x,y) to a calculated depth on a planar waveguide.

5. The optical integrated nanospectrometer of claim 3, wherein the super-grating is designed for monitoring specific wavelengths, where the wavelengths of interest are prerecorded in the hologram.

6. The optical integrated nanospectrometer of claim 1, wherein the optical integrated nanospectrometer is assembled as a single chip and further comprises a source of light spectrum.

7. The optical integrated nanospectrometer of claim 6, further comprising a focusing optical lens and an optical fiber, the optical integrated nanospectrometer comprising a laser-induced breakdown spectrometer, and said source of light spectrum comprising a pulsed laser coupled to the fiber by a narrowband concave grating for transporting light to the aforementioned analyte through the optical focusing lens.

8. The optical integrated nanospectrometer of claim 6, wherein the aforementioned source of light spectrum is a combination of several superluminescent laser-emitting diodes covering the entire spectral band and required for detecting absorption lines of an analyte.

9. The optical integrated nanospectrometer of claim 1, wherein the optical integrated nanospectrometer is an absorption nanospectrometer completely integrated as a single chip, wherein said at least one sensor comprises a bare optical fiber without a cladding for more convenient access to the analyte.

10. The optical integrated nanospectrometer of claim 8, wherein the superluminescent laser-emitting diodes are coupled with ridge waveguides into an optical fiber, said optical fiber having a coupling point and consisting of a core and cladding at the point of coupling and only of the core at the end of the optical fiber opposite to the point of coupling.

11. The optical integrated nanospectrometer of claim 1, wherein the optical integrated nanospectrometer is a Raman nanospectrometer completely integrated as a single chip and further comprises a stable and narrowband laser suitable for Raman spectroscopy, the nanospectrometer further comprising a bare ridge waveguide without an upper cladding and a planar slab waveguide, the stable and narrowband laser being coupled to the bare ridge waveguide while the bare ridge waveguide is wrapped around the planar slab waveguide and coupled thereto, the aforementioned super-grating being embedded into the slab waveguide and being illuminated.

12. The optical integrated nanospectrometer of claim 11, wherein the super-grating is transparent for the laser wavelength but reflects the light for all Raman-shifted wavelengths, which are focused by the super-grating on the detector arrays for conversion of light into electrical signals.

13. The optical integrated nanospectrometer of claim 1, wherein the optical integrated nanospectrometer is a folded nanospectrometer of high resolution, which is further provided with reflecting mirrors for reflecting light several times to provide multiple passes through the super-grating with longer optical paths for improving sensitivity of the nanospectometer.

14. The optical integrated nanospectrometer of claim 1, wherein the super-grating is apodized by removing some nano-features to provide a smooth profile of the effective waveguide refractive index and to prevent generation of side lobes.

15. The optical integrated nanospectrometer of claim 1, wherein the light inside the planar waveguide is processed by creating variation of the effective refractive index $\Delta n(x,y)$ of the planar waveguide in accordance with formula $$\Delta n(x,y) = \int\int f_{in}(x,y,\omega) f_{out}(x,y,\omega) d\omega$$

where $f_{in}(x,y,\omega)$ and $f_{out}(x,y,\omega)$ are Fourier components of desirable incoming and outgoing waves.

16. The optical integrated nanospectrometer of claim 15, wherein the effective refractive index $\Delta n(x,y)$ is approximated by a two-level binary function to simplify production and is further approximated by a composition of simplified binary structures.

17. The optical integrated nanospectrometer of claim 16, wherein the simplified binary structures are rectangular dashes of different length.

18. The optical integrated nanospectrometer of claim 16, wherein variation of the effective refractive index $\Delta n(x,y)$ is approximated by a composition of identical binary structures.

19. The optical integrated nanospectrometer of claim 16, wherein the variation of the effective refractive index $\Delta n(x,y)$ is approximated by a composition of simplified binary structures placed near maxima or minima of the original variation of the effective refractive index $\Delta n(x,y)$ given by the following formula:

$$\Delta n(x,y) = \int\int f_{in}(x,y,\omega) f_{out}(x,y,\omega) d\omega$$

where $f_{in}(x,y,\omega)$ and $f_{out}(x,y,\omega)$ are Fourier components of desirable incoming and outgoing waves.

* * * * *